(12) United States Patent
Toellner

(10) Patent No.: US 10,316,853 B2
(45) Date of Patent: Jun. 11, 2019

(54) FLUID PUMP HAVING A RADIALLY COMPRESSIBLE ROTOR

(71) Applicant: ECP ENTWICKLUNGSGESELLSCHAFT MBH, Berlin (DE)

(72) Inventor: Thomas Toellner, Berlin (DE)

(73) Assignee: ECP ENTWICKLUNGSGESELLSCHAFT MBH, Berlin (DE)

( * ) Notice: Subject to any disclaimer, the term of this patent is extended or adjusted under 35 U.S.C. 154(b) by 293 days.

(21) Appl. No.: 15/236,763

(22) Filed: Aug. 15, 2016

(65) Prior Publication Data

US 2017/0037860 A1 Feb. 9, 2017

Related U.S. Application Data

(63) Continuation of application No. 13/261,363, filed as application No. PCT/EP2011/000438 on Jan. 25, 2011, now Pat. No. 9,416,791.

(30) Foreign Application Priority Data

Jan. 25, 2010 (EP) .................................... 10075040

(51) Int. Cl.
| | |
|---|---|
| *F04D 29/00* | (2006.01) |
| *F04D 29/02* | (2006.01) |
| *F04D 3/00* | (2006.01) |
| *F04D 29/18* | (2006.01) |
| *F04D 29/24* | (2006.01) |

(Continued)

(52) U.S. Cl.
CPC ............. *F04D 29/026* (2013.01); *F04D 3/00* (2013.01); *F04D 3/02* (2013.01); *F04D 29/043* (2013.01); *F04D 29/046* (2013.01); *F04D 29/18* (2013.01); *F04D 29/181* (2013.01); *F04D 29/247* (2013.01); *F04D 29/528* (2013.01); *A61M 1/101* (2013.01); *A61M 1/1013* (2014.02); *A61M 1/1024* (2014.02); *A61M 1/1034* (2014.02); *A61M 1/122* (2014.02); *A61M 1/125* (2014.02)

(58) Field of Classification Search
CPC .. A61M 1/101; A61M 1/1024; A61M 1/1034; A61M 1/122; A61M 1/125; A61M 2205/0244; A61M 2205/0266; A61M 5/14236; F04D 19/00; F04D 29/181; F04D 29/528

See application file for complete search history.

(56) References Cited

U.S. PATENT DOCUMENTS

| | | |
|---|---|---|
| 3,510,229 A | 5/1970 | Smith et al. |
| 3,568,659 A | 3/1971 | Karnegis |

(Continued)

FOREIGN PATENT DOCUMENTS

| | | |
|---|---|---|
| CA | 1008330 | 4/1977 |
| CA | 2311977 | 12/2000 |

(Continued)

*Primary Examiner* — Amanda K Hulbert
(74) *Attorney, Agent, or Firm* — White & Case LLP

(57) ABSTRACT

To design the rotor (6, 6', 6", 6'", 60, 60') as compressible in the radial direction in a fluid pump, in particular for microinvasive medical use, said rotor is configured as stretchable in its longitudinal direction (16) by push elements and pull elements acting axially on it.

19 Claims, 5 Drawing Sheets

Related U.S. Application Data

Figure 1:
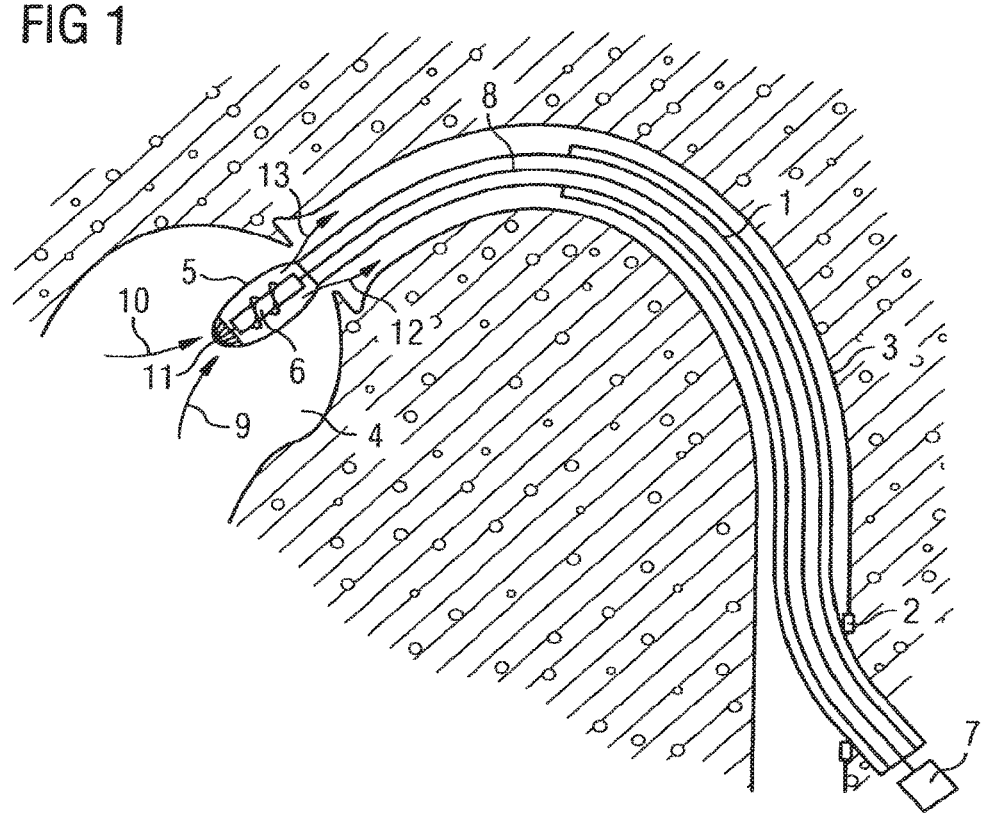

(60) Provisional application No. 61/297,858, filed on Jan. 25, 2010.

(51) Int. Cl.
  *F04D 3/02* (2006.01)
  *F04D 29/043* (2006.01)
  *F04D 29/046* (2006.01)
  *F04D 29/52* (2006.01)
  *A61M 1/10* (2006.01)
  *A61M 1/12* (2006.01)

(56) References Cited

U.S. PATENT DOCUMENTS

| | | |
|---|---|---|
| 3,802,551 A | 4/1974 | Somers |
| 3,812,812 A | 5/1974 | Hurwitz |
| 4,014,317 A | 3/1977 | Bruno |
| 4,207,028 A | 6/1980 | Ridder |
| 4,559,951 A | 12/1985 | Dahl et al. |
| 4,563,181 A | 1/1986 | Wijayarathna et al. |
| 4,679,558 A | 7/1987 | Kensey et al. |
| 4,686,982 A | 8/1987 | Nash |
| 4,747,821 A | 5/1988 | Kensey et al. |
| 4,749,376 A | 6/1988 | Kensey et al. |
| 4,753,221 A | 6/1988 | Kensey et al. |
| 4,801,243 A | 1/1989 | Norton |
| 4,817,613 A | 4/1989 | Jaraczewski et al. |
| 4,919,647 A | 4/1990 | Nash |
| 4,957,504 A | 9/1990 | Chardack |
| 4,969,865 A | 11/1990 | Hwang et al. |
| 4,995,857 A | 2/1991 | Arnold |
| 5,011,469 A | 4/1991 | Buckberg et al. |
| 5,040,944 A | 8/1991 | Cook |
| 5,042,984 A | 8/1991 | Kensey et al. |
| 5,052,404 A | 10/1991 | Hodgson |
| 5,061,256 A | 10/1991 | Wampler |
| 5,092,844 A | 3/1992 | Schwartz et al. |
| 5,097,849 A | 3/1992 | Kensey et al. |
| 5,108,411 A | 4/1992 | McKenzie |
| 5,112,292 A | 5/1992 | Hwang et al. |
| 5,113,872 A | 5/1992 | Jahrmarkt et al. |
| 5,117,838 A | 6/1992 | Palmer et al. |
| 5,118,264 A | 6/1992 | Smith |
| 5,145,333 A | 9/1992 | Smith |
| 5,151,721 A | 9/1992 | Allendorf et al. |
| 5,163,910 A | 11/1992 | Schwartz et al. |
| 5,169,378 A | 12/1992 | Figuera |
| 5,183,384 A | 2/1993 | Trumbly |
| 5,191,888 A | 3/1993 | Palmer et al. |
| 5,201,679 A | 4/1993 | Velte, Jr. et al. |
| 5,275,580 A | 1/1994 | Yamazaki |
| 5,373,619 A | 12/1994 | Fleischhacker et al. |
| 5,376,114 A | 12/1994 | Jarvik |
| 5,501,574 A | 3/1996 | Raible |
| 5,531,789 A | 7/1996 | Yamazaki et al. |
| 5,701,911 A | 12/1997 | Sasamine et al. |
| 5,749,855 A | 5/1998 | Reitan |
| 5,755,784 A | 5/1998 | Jarvik |
| 5,776,190 A | 7/1998 | Jarvik |
| 5,813,405 A | 9/1998 | Montano, Jr. et al. |
| 5,820,571 A | 10/1998 | Erades et al. |
| 5,851,174 A | 12/1998 | Jarvik et al. |
| 5,877,566 A | 3/1999 | Chen |
| 5,882,329 A | 3/1999 | Patterson et al. |
| 5,888,241 A | 3/1999 | Jarvik |
| 5,938,672 A | 8/1999 | Nash |
| 6,030,397 A | 2/2000 | Monetti et al. |
| 6,129,704 A | 10/2000 | Forman et al. |
| 6,152,693 A | 11/2000 | Olsen et al. |
| 6,168,624 B1 | 1/2001 | Sudai |
| 6,254,359 B1 | 7/2001 | Aber |
| 6,302,910 B1 | 10/2001 | Yamazaki et al. |
| 6,308,632 B1 | 10/2001 | Shaffer |
| 6,336,939 B1 | 1/2002 | Yamazaki et al. |
| 6,346,120 B1 | 2/2002 | Yamazaki et al. |
| 6,387,125 B1 | 5/2002 | Yamazaki et al. |
| 6,503,224 B1 | 1/2003 | Forman et al. |
| 6,506,025 B1 | 1/2003 | Gharib |
| 6,508,787 B2 | 1/2003 | Erbel et al. |
| 6,517,315 B2 | 2/2003 | Belady |
| 6,527,521 B2 | 3/2003 | Noda |
| 6,533,716 B1 | 3/2003 | Schmitz-Rode et al. |
| 6,537,030 B1 | 3/2003 | Garrison |
| 6,537,315 B2 | 3/2003 | Yamazaki et al. |
| 6,592,612 B1 | 7/2003 | Samson et al. |
| 6,652,548 B2 | 11/2003 | Evans et al. |
| 6,719,791 B1 | 4/2004 | Nusser et al. |
| 6,790,171 B1 | 9/2004 | Grundeman et al. |
| 6,860,713 B2 | 3/2005 | Hoover |
| 6,945,977 B2 | 9/2005 | Demarais et al. |
| 6,981,942 B2 | 1/2006 | Khaw et al. |
| 7,022,100 B1 | 4/2006 | Aboul-Hosn et al. |
| 7,027,875 B2 | 4/2006 | Siess et al. |
| 7,054,156 B2 | 5/2006 | Espinoza-Ibarra et al. |
| 7,074,018 B2 | 7/2006 | Chang |
| 7,179,273 B1 | 2/2007 | Palmer et al. |
| 7,393,181 B2 | 7/2008 | McBride et al. |
| 7,467,929 B2 | 12/2008 | Nusser et al. |
| 7,731,675 B2 | 6/2010 | Aboul-Hosn et al. |
| 7,841,976 B2 | 11/2010 | McBride et al. |
| 7,927,068 B2 | 4/2011 | McBride et al. |
| 7,934,909 B2 | 5/2011 | Nuesser et al. |
| 8,079,948 B2 | 12/2011 | Shifflette |
| 2002/0094273 A1 | 7/2002 | Huang |
| 2002/0123661 A1 | 9/2002 | Verkerke et al. |
| 2003/0135086 A1 | 7/2003 | Khaw et al. |
| 2003/0231959 A1 | 12/2003 | Snider |
| 2004/0044266 A1 | 3/2004 | Siess et al. |
| 2004/0046466 A1 | 3/2004 | Siess et al. |
| 2004/0093074 A1 | 5/2004 | Hildebrand et al. |
| 2004/0215222 A1 | 10/2004 | krivoruchko |
| 2004/0215228 A1 | 10/2004 | Simpson et al. |
| 2005/0101200 A1 | 5/2005 | Townsend |
| 2006/0008349 A1 | 1/2006 | Khaw |
| 2006/0062672 A1 | 3/2006 | McBride et al. |
| 2006/0195004 A1 | 8/2006 | Jarvik |
| 2007/0270875 A1 | 11/2007 | Bacher et al. |
| 2008/0073983 A1 | 3/2008 | Krajcir |
| 2008/0103591 A1 | 5/2008 | Siess |
| 2008/0132747 A1 | 6/2008 | Shifflette |
| 2008/0132748 A1 | 6/2008 | Shifflette |
| 2008/0262584 A1 | 10/2008 | Bottomley et al. |
| 2008/0306327 A1 | 12/2008 | Shifflette |
| 2009/0060743 A1 | 3/2009 | McBride et al. |
| 2009/0093764 A1* | 4/2009 | Pfeffer .............. A61M 1/1031 604/151 |
| 2009/0093796 A1 | 4/2009 | Pfeffer |
| 2010/0041939 A1 | 2/2010 | Siess |
| 2010/0268017 A1 | 10/2010 | Siess |
| 2011/0071338 A1 | 3/2011 | McBride et al. |
| 2011/0236210 A1 | 9/2011 | McBride et al. |
| 2011/0238172 A1 | 9/2011 | Akdis |
| 2011/0257462 A1 | 10/2011 | Rodefeld et al. |
| 2011/0275884 A1 | 11/2011 | Scheckel |
| 2012/0039711 A1 | 2/2012 | Roehn |
| 2012/0039713 A1 | 2/2012 | Shifflette |
| 2012/0041254 A1 | 2/2012 | Scheckel |
| 2012/0046648 A1 | 2/2012 | Scheckel |
| 2012/0093628 A1 | 4/2012 | Liebing |
| 2012/0101455 A1 | 4/2012 | Liebing |
| 2012/0142994 A1 | 6/2012 | Toellner |
| 2012/0184803 A1 | 7/2012 | Simon et al. |
| 2012/0224970 A1 | 9/2012 | Schumacher et al. |
| 2012/0234411 A1 | 9/2012 | Scheckel |
| 2012/0237353 A1 | 9/2012 | Schumacher et al. |
| 2012/0237357 A1 | 9/2012 | Schumacher et al. |
| 2012/0264523 A1 | 10/2012 | Liebing |
| 2012/0265002 A1 | 10/2012 | Roehn et al. |
| 2012/0294727 A1 | 11/2012 | Roehn |
| 2012/0301318 A1 | 11/2012 | Er |
| 2012/0308406 A1 | 12/2012 | Schumacher |
| 2013/0019968 A1 | 1/2013 | Liebing |
| 2013/0041202 A1 | 2/2013 | Toellner |

(56) References Cited

U.S. PATENT DOCUMENTS

| | | |
|---|---|---|
| 2013/0060077 A1 | 3/2013 | Liebing |
| 2013/0066139 A1 | 3/2013 | Wiessler et al. |
| 2013/0085318 A1 | 4/2013 | Toellner |
| 2013/0177409 A1 | 7/2013 | Schumacher et al. |
| 2013/0177432 A1 | 7/2013 | Toellner et al. |
| 2013/0204362 A1 | 8/2013 | Toellner et al. |
| 2013/0237744 A1 | 9/2013 | Pfeffer et al. |
| 2014/0039465 A1 | 2/2014 | Schulz et al. |

FOREIGN PATENT DOCUMENTS

| | | |
|---|---|---|
| CA | 2701809 | 4/2009 |
| CA | 2701810 | 4/2009 |
| DE | 2207296 | 8/1972 |
| DE | 2113986 | 9/1972 |
| DE | 2233293 | 1/1973 |
| DE | 2613696 | 10/1977 |
| DE | 4124299 | 1/1992 |
| DE | 69103295 | 12/1994 |
| DE | 69017784 | 11/1995 |
| DE | 19535781 | 3/1997 |
| DE | 19711935 | 4/1998 |
| DE | 29804046 | 4/1998 |
| DE | 69407869 | 4/1998 |
| DE | 69427390 | 9/2001 |
| DE | 100 59 714 | 5/2002 |
| DE | 10108810 | 8/2002 |
| DE | 10155011 | 5/2003 |
| DE | 69431204 | 8/2003 |
| DE | 10336902 | 8/2004 |
| DE | 102010011998 | 9/2010 |
| EP | 0364293 | 4/1990 |
| EP | 0480102 | 4/1992 |
| EP | 0560000 | 9/1993 |
| EP | 0629412 | 12/1994 |
| EP | 0768091 | 4/1997 |
| EP | 0884064 | 12/1998 |
| EP | 0914171 | 5/1999 |
| EP | 0916359 | 5/1999 |
| EP | 951302 | 10/1999 |
| EP | 1061968 | 12/2000 |
| EP | 1066851 | 1/2001 |
| EP | 1114648 | 7/2001 |
| EP | 1337288 | 8/2003 |
| EP | 1651290 | 5/2006 |
| EP | 1019117 | 11/2006 |
| EP | 2047872 | 4/2009 |
| EP | 2218469 | 8/2010 |
| EP | 2229965 | 9/2010 |
| EP | 2301598 | 3/2011 |
| EP | 2308524 | 4/2011 |
| EP | 2343091 | 7/2011 |
| EP | 2345440 | 7/2011 |
| EP | 2366412 | 9/2011 |
| EP | 2497521 | 9/2012 |
| EP | 2606919 | 6/2013 |
| EP | 2606920 | 6/2013 |
| EP | 2607712 | 6/2013 |
| GB | 2405677 | 2/1934 |
| GB | 2239675 | 7/1991 |
| RU | 2229899 | 6/2004 |
| WO | WO-9202263 | 2/1992 |
| WO | WO-9302732 | 2/1993 |
| WO | WO-9303786 | 3/1993 |
| WO | WO-9314805 | 8/1993 |
| WO | WO-94001148 | 1/1994 |
| WO | WO-9405347 | 3/1994 |
| WO | WO-9409835 | 5/1994 |
| WO | WO-9420165 | 9/1994 |
| WO | WO-9523000 | 8/1995 |
| WO | WO-9618358 | 6/1996 |
| WO | WO-9625969 | 8/1996 |
| WO | WO-9744071 | 11/1997 |
| WO | WO-9853864 | 12/1998 |
| WO | WO-9919017 | 4/1999 |
| WO | WO-9944651 | 9/1999 |
| WO | WO-0027446 | 5/2000 |
| WO | WO-0043054 | 7/2000 |
| WO | WO-0062842 | 10/2000 |
| WO | WO-2001007760 | 2/2001 |
| WO | WO-2001007787 | 2/2001 |
| WO | WO-2001083016 | 11/2001 |
| WO | WO-2003057013 | 7/2003 |
| WO | WO-2003103745 | 12/2003 |
| WO | WO-2005002646 | 1/2005 |
| WO | WO-2005016416 | 2/2005 |
| WO | WO-2005021078 | 3/2005 |
| WO | WO-2005030316 | 4/2005 |
| WO | WO-2005032620 | 4/2005 |
| WO | WO-2005081681 | 9/2005 |
| WO | WO-2006020942 | 2/2006 |
| WO | WO-2006034158 | 3/2006 |
| WO | WO-2006051023 | 5/2006 |
| WO | WO-2006133209 | 12/2006 |
| WO | WO-2007003351 | 1/2007 |
| WO | WO-2007103390 | 9/2007 |
| WO | WO-2007103464 | 9/2007 |
| WO | WO-2007112033 | 10/2007 |
| WO | WO-2008017289 | 2/2008 |
| WO | WO-2008034068 | 3/2008 |
| WO | WO-2008054699 | 5/2008 |
| WO | WO-2008106103 | 9/2008 |
| WO | WO-2008116765 | 10/2008 |
| WO | WO-2008124696 | 10/2008 |
| WO | WO-2008137352 | 11/2008 |
| WO | WO-2008137353 | 11/2008 |
| WO | WO-2009015784 | 2/2009 |
| WO | WO-2009029959 | 3/2009 |
| WO | WO-2009073037 | 6/2009 |
| WO | WO-2010133567 | 11/2010 |
| WO | WO-2013034547 | 3/2013 |
| WO | WO-2013092971 | 6/2013 |
| WO | WO-2013093001 | 6/2013 |
| WO | WO-2013093058 | 6/2013 |

* cited by examiner

FLUID PUMP HAVING A RADIALLY COMPRESSIBLE ROTOR

CROSS-REFERENCE TO RELATED APPLICATIONS

This application is a continuation of U.S. patent application Ser. No. 13/261,363, which entered the national stage on Oct. 19, 2012 and which is a United States National Stage filing under 35 U.S.C. § 371 of International Application No. PCT/EP2011/000438, filed Jan. 25, 2011, which claims the benefit of U.S. Provisional Patent Application No. 61/297,858, filed Jan. 25, 2010, and European Patent Application No. 10075040.5, filed Jan. 25, 2010, the contents of all of which are incorporated by reference herein in their entirety. International Application No. PCT/EP2011/000438 was published under PCT Article 21(2) in English.

The invention is in the field of mechanical engineering, in particular of micromechanics, and specifically relates to fluid pumps having a rotor and at least one impeller blade for the predominantly axial conveying of a fluid.

Pumps of this kind can be used in different technical fields, particularly where deployment locations are difficult to access and a compressible rotor can be brought onto site in compressed form and can there be expanded for efficient operation.

A particularly advantageous application is in the field of medicine where pumps of this kind can be introduced in particularly small construction into the body of a patient, for example through blood vessels, can be expanded at the deployment location, preferably in a ventricle, and can be operated there.

To remove the pump, it can usually be compressed again and removed through a sluice.

Corresponding compressible pumps are already known in different constructions.

A rotor is, for example, known from WO 03/103745 A2 which has a smaller diameter in a compressed state than in an expanded state and which has an unfoldable rotor blade which unfolds in operation by the fluid counterpressure of the fluid.

WO 03/103475 moreover discloses a rotor which has elements which are axially displaceable with respect to one another and whose mutual displacement accompanies the expansion and compression of a cage surrounding the rotor in the manner of a housing.

Rotors are moreover known from the prior art whose impeller blades are unfoldable for operation and have joints or elastic support parts for this purpose. The use of so-called memory alloys such as Nitinol is in particular known which adopt different geometrical shapes in dependence on the environmental temperature and thereby allow a subsequent deformation of the rotor after the introduction into a body.

A fluid pump is known from WO 99/44651 having a compressible rotor which has a compressible coil which is covered by membrane, comprises a memory alloy and is held together axially by an elastic band. The coil can be compressed by radial pressure thereon.

A fluid pump is known from WO 94/05347 having a rotor which carries conveying elements and is fixedly connected to a shaft, with a sleeve moreover being axially displaceably arranged on the shaft by whose displacement a housing surrounding the rotor can be stretched lengthwise and thus radially compressed. A relative movement of the sleeve to the shaft is converted by a lever mechanism into a radial erection of the conveying elements or into a folding down onto the shaft.

A compressible propeller pump with a rotor is known from WO 99/44651 having a helicoidal coil and an elastic band spanned centrally and coaxially therein as well as a membrane spanned between the named elements as an impeller blade.

Experience has shown that complex constructions for such pumps are also difficult to realize and to operate reliably with the desired service lives due to the small construction.

It is therefore the underlying object of the present invention against this background to provide a fluid pump of the initially named kind which allows a reliable function of the pump both on the introduction and removal and in regular operation with a simple construction design and at low costs.

The object is achieved by the features of the invention in accordance with claim 1.

In this respect, the fluid pump in accordance with the invention provides a drivable rotor which is rotatable about its longitudinal axis and which has at least one impeller, with the rotor at least partly comprising an elastically compressible and expandable material and being elastically stretchable in the direction of its longitudinal axis by elements acting axially on it.

Provision is moreover made in this respect that a push-element and a pull-element engage at different ends of the rotor and/or of a housing of the fluid pump.

A transverse contraction can, on the one hand, be directly realized by the elastic stretchability in the longitudinal direction with such a material-elastic rotor which can, for example, partly comprise an elastomer or a foam. However, different mechanisms within the rotor can also be set into motion by the longitudinal stretching which result in a transverse compression or in an easier transverse compressibility. Provision can e.g. be made for this purpose that the impeller blades are also stretched in the longitudinal direction of the rotor in that they are connected to a hub over a certain extent in the longitudinal direction of said hub. In the non-stretched state, the impeller blades can have a concave or convex or folded form or correspondingly formed support structures in their interior which are stretched by the longitudinal stretching of the rotor. Such geometrical shapes can give the blades additional stability with respect to the fluid pressure in operation, but also with respect to a radial compression, in the non-stretched state. If such structures are elongated by longitudinal stretching of the rotor, a facilitated deformability of the impeller blades results so that the rotor as a whole either becomes more easily radially compressible or automatically at least compresses a little on a longitudinal stretching.

A corresponding facilitation of the radial compressibility can then optionally be utilized by additional mechanisms of the radial compression, for example on moving into a sluice.

The described construction with a connection between the impeller blades and the hub extended in the longitudinal direction is moreover of simple construction to the extent that the rotor and the impeller blades can be manufactured in one piece, for example, cast or vulcanized.

The rotor can advantageously be arranged at the distal end of a hollow catheter for the medical deployment of a fluid pump in accordance with the invention in order to be able to transport it with said hollow catheter through a bloodstream into a ventricle, for example.

Provision can advantageously be made in this case that a pull can be applied in mutually opposite directions to both ends of the rotor by two elements mutually movable and extending along the catheter. The rotor can thus be extended from the proximal end of the catheter along the catheter by different mutually displaceable elements.

Provision can advantageously be made in this respect that one of the elements is a jacket and the other element is a core extending in the jacket. On the provision of a jacket and of a core extending therein, these two elements can support one another against outward kinking. A pull can, on the one hand, by applied by means of the jacket and a pressure in the longitudinal direction can be applied by means of the core, or vice versa.

The hollow catheter can advantageously itself serve as a jacket and, optionally, a drive shaft extending therein can also serve as a core.

Alternatively or additionally to this, however, lines can also be introduced at the outer circumference of the catheter which, with a corresponding stiffness, can transmit both a pull and a compression in the longitudinal direction or corresponding pull-movements and push-movements.

These lines can be introduced along the catheter up to the sluice through which the catheter is introduced into the body and can extend further to the exterior of the body and can be fastened in a fastening ring there so that the lines can be comfortably operated from outside the patient's body.

Provision can be made for the more specific embodiment of the invention that the proximal end of the rotor is connected to the core and the distal end of the rotor is connected to a housing of the rotor in a pull-resistant manner and that the housing is connected in a pressure-resistant manner to the jacket. In this case, the core can apply a pull to the rotor at its proximal end, whereas the other, distal, end of the rotor is held in a housing, for example, in a pull-resistant rotary bearing, which applies a pull in a direction opposite to the core to the rotor which can be realized by a support of the housing at the distal end of the hollow catheter/of the sleeve as a holding force. A compressive force then has to be applied to the sleeve along the catheter and a corresponding pulling force has to be applied to the core.

Provision can also advantageously be made that the proximal end of the rotor is connected directly, or indirectly via the housing, to the sleeve in a pull-resistant manner and that the distal end of the rotor is connected directly, or indirectly via the housing, to the core in a pressure-resistant manner. In this case, a pull-force is applied by the distal end of the jacket to the proximal end of the rotor, for example by a pull-resistant rotary bearing, whereas a pull-force is applied in the distal direction to the distal end of the rotor by the core which transmits a corresponding push-force. The core can for this purpose extend, for example, through the rotor and be connected to the rotor at its distal end. The core can, for example, be formed by a drive shaft of the rotor.

A further embodiment of the invention provides that the rotor is surrounded by a housing likewise stretchable in the direction of the longitudinal axis. In this case, the rotor can in each case be connected rotatably, but in a pull-resistant manner, at its two ends to the housing, e.g. in that the rotor is journalled at both sides in the housing in pull-resistant rotary bearings. If a longitudinal stretching is then exerted onto the housing, it is transmitted directly to the rotor. The rotor is thus either compressed directly in the radial direction or it is at least more easily compressible.

Provision can particularly advantageously be made in this respect that the housing automatically undergoes a longitudinal stretching parallel to the longitudinal axis in the case of a transverse compression substantially perpendicular to the longitudinal axis. Provision can advantageously be made in this respect that the housing has a bulbous shape with an inner space sufficient for the expanded rotor in the state in which no forces act on it in the longitudinal direction.

In this case, a longitudinal stretching of the housing and thus a longitudinal stretching of the rotor, associated with a transverse contraction or facilitation of the compressibility of the rotor, can be achieved by application of a radial compression onto the housing, that is, for example, by moving the housing into a funnel-shaped sluice. For this purpose, a corresponding sluice which generates a corresponding radial compression on the withdrawal of the pump housing can be provided, for example, at the end of the hollow catheter. A sluice can, however, also be provided which surrounds the hollow catheter as such and into which the hollow catheter can be withdrawn for the compression of the housing. A corresponding sluice can have an inflow funnel for the pump housing for this purpose.

The invention will be shown and subsequently described in the following with reference to an embodiment in a drawing.

There are shown

Figure 2:
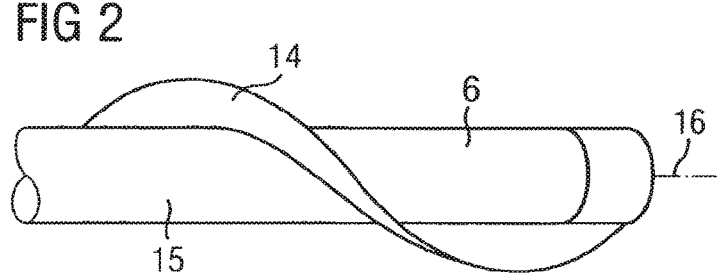
Figure 3:
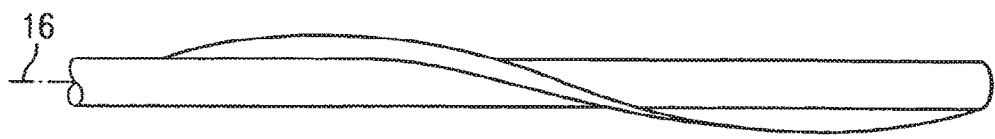
Figure 4:
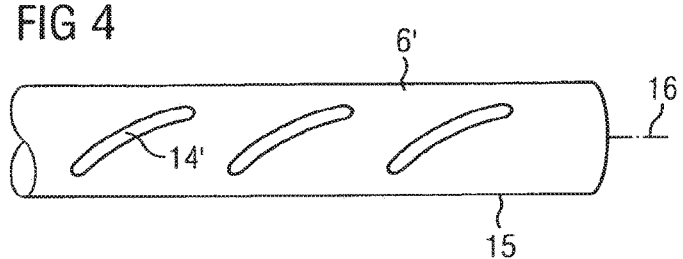
Figure 5:
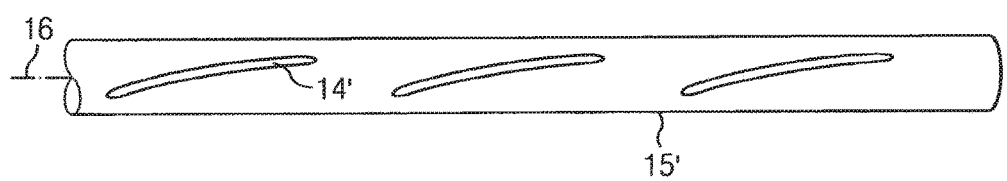
Figure 6:
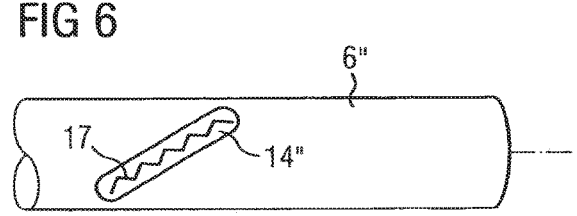
Figure 7:
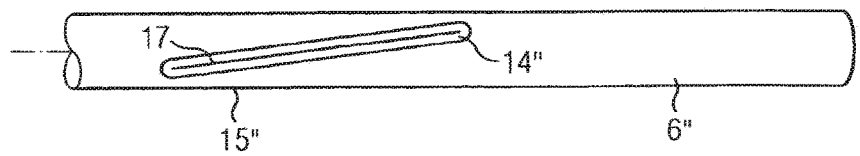
Figure 8:
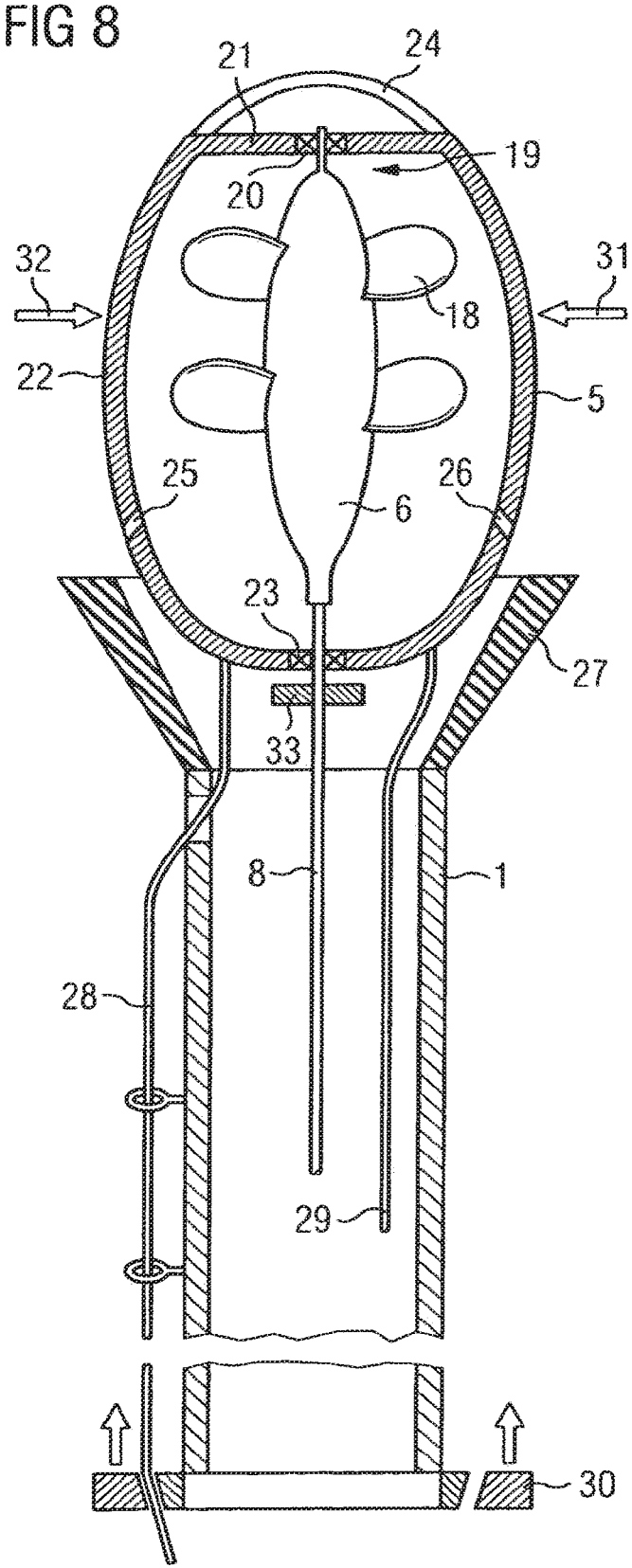
Figure 9:
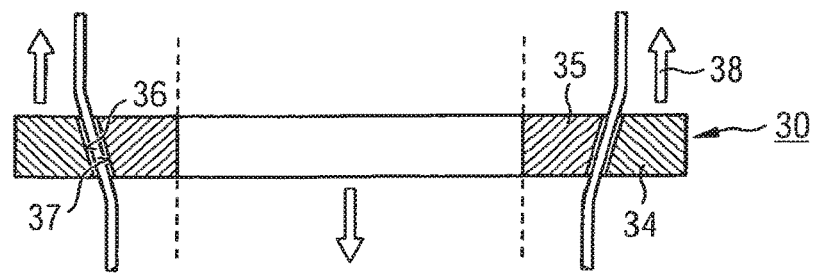
Figure 10:
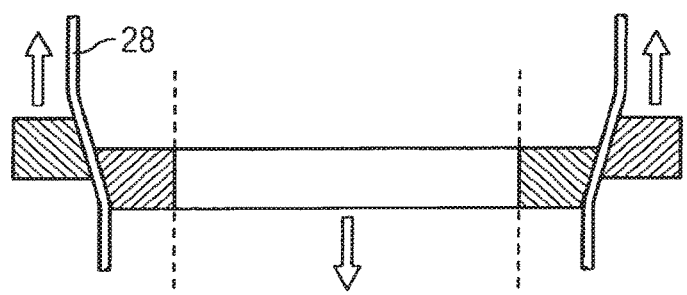
Figure 11:
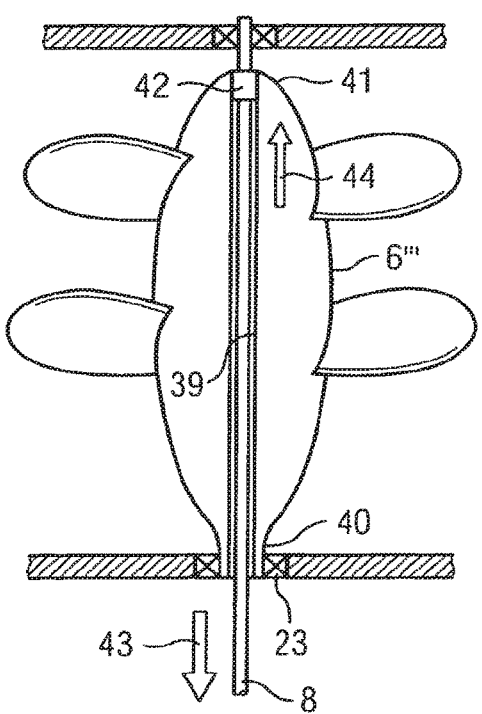
Figure 12:
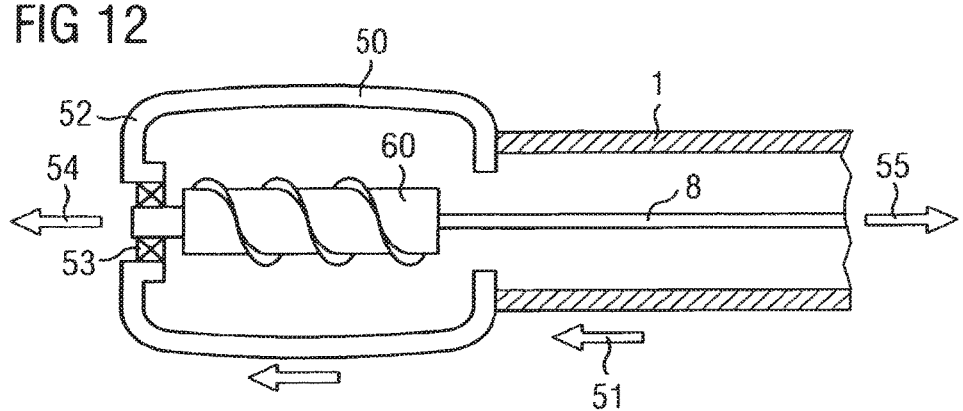
Figure 13:
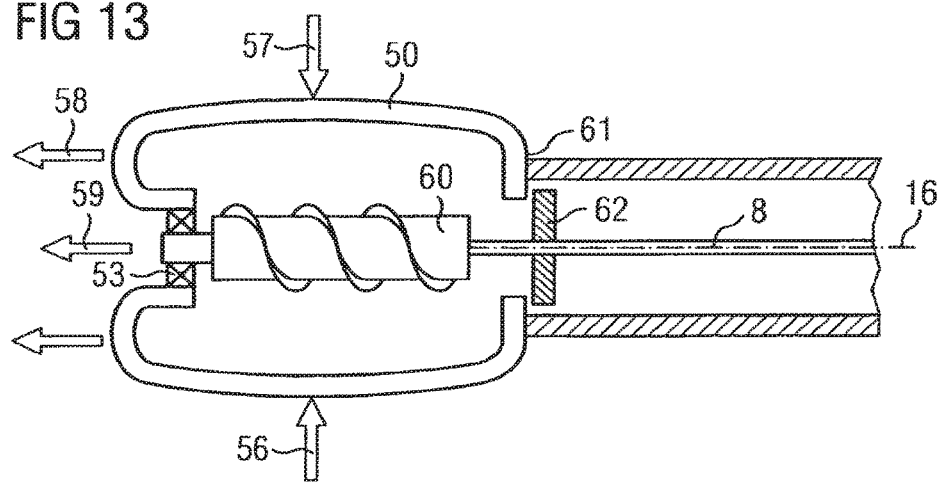
Figure 14:
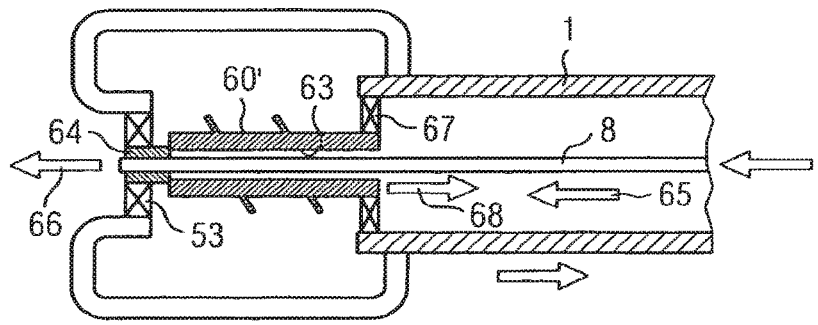

FIG. 1 schematically in an overview, the use of a micropump in accordance with the invention in a ventricle;

FIG. 2 a three-dimensional view of a rotor in accordance with the invention in a non-stretched form;

FIG. 3 the view of the rotor of FIG. 2 in a longitudinally stretched form;

FIG. 4 a view of a further rotor in non-stretched form;

FIG. 5 the rotor of FIG. 4 in a form stretched in the longitudinal direction;

FIG. 6 a further rotor in a three-dimensional view in a non-stretched form;

FIG. 7 the rotor of FIG. 6 in a form stretched in the longitudinal direction;

FIG. 8 highly magnified in a longitudinal section, the structure of a micropump in accordance with the invention with the end of a hollow catheter;

FIG. 9 a fastening apparatus for lines which run along the catheter for manipulating the pump;

FIG. 10 the arrangement of FIG. 9 in a wedged state;

FIG. 11 a longitudinal section through a rotor in whose central hollow space a drive shaft extends;

FIG. 12 schematically in a first arrangement, the components of a pump which participate in the application of a longitudinal pull onto the rotor;

FIG. 13 a similar arrangement as in FIG. 12 with another principle for the application of the pull; and FIG. 14 a third arrangement for applying a longitudinal pull to a rotor using a further principle.

FIG. 1 shows a hollow catheter 1 which is introduced through a sluice 2 into a blood vessel 3 of a human body and which is inserted there up to the ventricle 4. At the distal end of the hollow catheter 1, a pump 5 is fastened having a rotor 6 which rotates about its longitudinal axis and thus conveys blood axially out of the ventricle 4 into the blood vessel 3.

The rotor is for this purpose drivable by a motor 7 via a shaft 8 at a high speed, typically between 10,000 and 50,000 revolutions per minute.

Blood is sucked in axially by the rotation of the rotor 6 in the direction of the arrows 9, 10 through the intake openings 11 of the pump and is expelled again in the direction of the arrows 12, 13 within the blood vessel 3. The activity of the heart in the conveying of blood is thereby replaced or supplemented.

The pump 5 has a housing surrounding the rotor 6 and is radially compressible as a whole with respect to the diameter for insertion into the blood vessel 3.

Once the pump 5 has reached the ventricle 4, it can be radially expanded in that both the housing and the rotor 6 are expanded to achieve a higher performance capability of the pump by erecting the rotor blades.

It is the object of the present invention to achieve a radial compressibility of the rotor 6 which is as easy and as simple as possible.

To illustrate the function of the invention, a rotor 6 having a helically revolving impeller blade 14 will first be looked at with reference to FIG. 2. The impeller blade 14 must have a certain minimum stiffness in order not to be folded down onto the hub 15 of the rotor 6 by the fluid counterpressure on the conveying of a fluid.

This stiffness generally makes it difficult to achieve a radial compression or a placing of the impeller blade 14 onto the hub 15 to reduce the diameter of the rotor on the installation of the pump.

In FIG. 3, the rotor from FIG. 2 is shown in a form stretched in the longitudinal direction. The hub body 15 can, just like the impeller blades, for example, comprise rubber or another elastomer or a foam or another compressible and expandable material and is automatically compressed on a longitudinal stretching of the rotor by the general maintenance of volume.

At the same time, the dimensions of the impeller blade 14 transversely to the longitudinal direction 16 reduce so that the total dimensions of the rotor 6 transverse to the longitudinal direction 16 reduce due to a simultaneous radial compression of the hub body 15 and of the impeller blade 14. The rotor can be transported substantially more easily through a narrow blood vessel in this state than in the expanded state without a longitudinal stretching of the rotor. The total diameter of the rotor is thus easily reduced. In addition, the longitudinal stretching can have an effect on the impeller blade.

FIG. 4 shows another embodiment of the rotor 6' having impeller blades 14' which are made concave or curved in cross-section to provide the individual impeller blade with additional stability with respect to an inward kinking due to the fluid counterpressure.

If the corresponding rotor 6' is stretched in the longitudinal direction 16, the illustration as shown in FIG. 5 results in which the diameter of the hub body 15' is reduced and simultaneously the impeller blades 14' are pulled longitudinally in the longitudinal direction 16. The concave form of the impeller blades 14° is hereby completely or almost completely eliminated so that the stability of each individual impeller blade with respect to a kink movement in the peripheral direction of the rotor is much reduced. The stability of the impeller blades is thus reduced and a radial compression by external effect, for example, on a compression of the housing surrounding the rotor is simplified.

In FIG. 6, another principle of rotor design is shown which can be used in addition or alternatively to the above-described installations, with a rotor 6" being equipped with impeller blades 14" which, in their interior, have a stiffening structure 16 in the form of a metal sheet or another flat material kinked in the manner of saw teeth in cross-section. This kinked reinforcement material stiffens the impeller blade 14" greatly with respect to kinking.

If the rotor 6" is pulled lengthways, the situation as shown in FIG. 7 results, with the impeller blade 14" being pulled lengthways and thus the angle of engagement being reduced and with the reinforcement structure 17 simultaneously being pulled longitudinally by the stretching in the longitudinal direction up to the complete elimination of the kink.

The impeller blade 14" can hereby be folded onto the hub body 15" a lot more easily and the rotor 6" is thus radially compressed with respect to the hub body, on the one hand, and can be further compressible even more easily with respect to the impeller blades.

FIG. 8 shows a fluid pump 6 having a rotor 6 which has impeller blades 18 in a longitudinal section. It is schematically shown that the rotor 6 is rotatably journalled in a distal bearing 20 at its distal end 19. The bearing 20 is fastened to struts 21 of the pump housing 22.

The rotor 6 is rotatably journalled in a proximal bearing 23 at its proximal end, and indeed by means of a shaft 8 or by means of a stiffened connector piece of the shaft 8 at the rotor 6.

The fluid pump 5 sucks in liquid through an intake cage 24 and expels it again through the openings 25, 26. The pump 5 is arranged at the distal end of a hollow catheter 1 through which the drive shaft 8 extends in the longitudinal direction. The hollow catheter 1 has an inflow sluice 27 in the form of a funnel at its end and the housing 5 can be pulled into said inflow sluice for the removal of the pump from a patient's body. A pulling movement can, for example, be applied to the housing 5 by means of the lines 28, 29, with the lines 28 being guided in holders at the outer side of the hollow catheter, while the line 29 is shown as extending in the interior of the hollow catheter.

When the guide of the lines 28, 29 is tight enough, they cannot only be transferred by a pulling movement, but also by a pushing in the longitudinal direction.

The lines 28, 29 can, as shown at the bottom of FIG. 8, be held at the proximal end of the hollow catheter 1, for example in a clamping ring 30, which can be displaced or also rotated and fixed as a whole for manipulating the pump 5 along the catheter. The corresponding lines 28 are clamped in the clamping ring 30.

In the example shown, the bearing 20 is a pull-resistant rotary bearing so that the distal end of the rotor 6 is not only rotatably journalled in this bearing, but is also held in the longitudinal direction.

The proximal bearing 23 allows a movement of the shaft 8 or of a shaft prolongation in the longitudinal direction so that no pull-resistant connection is present there.

If a pull is exerted at the drive shaft 8 in the longitudinal direction from the proximal end of the hollow catheter, the rotor 6 is subjected to a longitudinal stretching which results in a transverse compression.

It is also conceivable to exert radial pressure onto the housing 5 in the direction of the arrows 31, 32 and thus to achieve a longitudinal stretching of the housing which can be transmitted to the rotor 6 in that the housing abuts the abutment 33 fixedly connected to the shaft 8 or at least fixed in the longitudinal direction with respect to the shaft 8 in the region of the proximal bearing 23 and also pulls the rotor lengthways on a further longitudinal stretching of the housing.

An automatic transverse compression of the rotor thereby results so that the rotor can simply also be compressed as part of the compression of the housing 5.

In FIG. 9, the function of the clamping ring 30 is shown in a schematic manner which has an outer part ring 34 and an inner part ring 35, each of which part rings have conical boundary surfaces 36, 37. If the outer part ring 34 is moved in the direction of the arrow 38 with respect to the inner part ring 35, the image shown in FIG. 10 results in which the conical surfaces 36, 37 come into contact with one another and wedge together. The lines 28 arranged between them are clamped in this connection and are fixed in the longitudinal direction.

The total clamping ring 30 can then be moved for manipulating the lines 28.

The diameter-reduced state and the expanded state could in each case also be locked independently of one another with the aid of an apparatus which is not further embodied.

FIG. 11 schematically shows a special embodiment of the rotor 6''' which has a central hollow space 39 through which the drive shaft 8 extends lengthways from the proximal end 40 of the rotor to the distal end 41. The drive shaft 8 is connected via a mount body 42 in a rotationally fixed and pull-resistant manner to the rotor at the distal end 41 so that the rotor 6''' can be driven via the shaft 8 from the proximal end 40. At the same time, however, the rotor 6''' can be connected in a pull-resistant manner to the shaft 8 at the proximal end 40 in the pulling direction which is indicated by the arrows 43.

The rotor is journalled there in a rotatable and pull-resistant manner in the proximal bearing 23 so that, when a pressure is applied onto the shaft 8 in the direction of the arrow 44, the rotor is pulled lengthways between the mount body 42 and the bearing 23. The rotor 6''' can hereby be compressed in the transverse direction.

FIGS. 12, 13 and 14 generally show different principles according to which a longitudinal pull can be applied to a rotor in similar embodiments. In this respect, the housing is designated by 50 in FIG. 12. Said housing surrounds the rotor 60 and is supported on the distal end of the hollow catheter 1.

A pressure can thus be transmitted in the direction of the arrow 51 via the hollow catheter 1 onto the housing 50 whose distal end 52 can exert a pull onto the rotor 60 in the direction of the arrow 54 via the pull-resistant bearing 53.

The drive shaft 8 is rotationally fixedly connected to the proximal end of the rotor 60. Said proximal end can moreover, which is not shown in detail, be axially displaceably rotatably journalled at the housing 50 or at the hollow catheter 1. If a pull is exerted onto the drive shaft 8 in the direction of the arrow 55 and if the hollow catheter is simultaneously supported, the rotor 60 is stretched in the longitudinal direction.

It is shown with reference to FIG. 13 that a transverse pressure can also be exerted onto the housing 50 perpendicular to the longitudinal direction, shown by the arrows 56, 57, said transverse pressure resulting in a longitudinal stretching of the housing 50 in the direction of the longitudinal axis 16 due to the bulbous embodiment of the housing which is stiff to a certain extent. The housing can comprise a hose, for example made from an elastomer or from longitudinal bars which are covered by a membrane or are surrounded by a deformable hose. The distal end of the housing 50 expands in the direction of the arrow 58. A corresponding pull is exerted onto the rotor 60 in the direction of the arrow 59 via the pull-resistant rotary bearing 53. The housing 50 lengthens so far in the direction of the longitudinal axis 16 until its proximal end 61 abuts the abutment 62 which is non-displaceably connected to the drive shaft 8. On a corresponding further expansion of the housing 50 in the longitudinal direction, a pull is exerted onto the drive shaft 8 by means of the abutment 62 which results in a longitudinal stretching of the rotor 60. Alternatively, the abutment 62 can also be omitted provided that a pull is applied to the proximal end of the rotor by means of the drive shaft 8.

FIG. 14 shows that a rotor 60' having a central hollow space 63 can be used, with the drive shaft 8 passing through the hollow space 63 from its proximal side up to the distal end. The drive shaft 8 is there connected in a pull-resistant manner to a connection element 64 which can in turn be journalled in a rotatable and pull-resistant manner in the bearing 53. The bearing can be made as a pull-resistant or as a non-pull resistant bearing.

A pressure can be exerted onto the rotor 60' by means of the drive shaft 8 in the direction of the arrow 65. A pull is correspondingly exerted via the connection element 64 onto the distal end of the rotor 60' in the direction of the arrow 66. At the proximal end of the rotor 60', the latter is rotatably journalled in a pull-resistant manner in a bearing 67 which is in turn non-displaceably fastened to the distal end of the hollow catheter 1. A pull can correspondingly be applied via this bearing 67 onto the proximal end of the rotor in the direction of the arrow 68, whereby the rotor 60' as a whole is stretched in the longitudinal direction. Alternatively, the rotor can also be rotatably journalled at its proximal end in a pull-resistant manner in the housing and the housing can be axially fixed with respect to the catheter.

The rotor is compressed or is at least more simply compressible in the transverse direction due to the different technical possibilities described in connection with the invention of applying a longitudinal stretching onto the rotor. Corresponding impeller blades can likewise also be stretched and/or brought into a more easily compressible state. The invention thus allows a better compressibility of the rotor and of the fluid pump as a whole.

The invention claimed is:

1. An intravascular fluid pump comprising:
   a drivable rotor which is rotatable about a longitudinal axis, wherein the rotor at least partly comprises an elastically compressible and expandable material;
   at least one impeller blade disposed on the rotor, wherein the rotor and the at least one impeller blade are formed from the same material, and
   a hollow tube configured to compress the rotor when the rotor is pulled into the hollow tube;
   wherein the rotor is held in tension by a first element coupled to a distal end of the rotor and a second element coupled to a proximal end of the rotor.

2. The fluid pump of claim 1, wherein the rotor is elastically stretchable in the direction of the longitudinal axis between the first element and the second element.

3. The fluid pump of claim 2, wherein the first element and the second element are configured to elastically stretch the rotor by applying force in mutually opposite directions at different ends of the rotor.

4. The fluid pump of claim 3, wherein the rotor has an axially through going hub, and wherein at least one impeller blade is coupled to the hub over at least a part of a length of the hub.

5. The fluid pump of claim 4, wherein the rotor changes a dimension in dependence on the length of the rotor.

6. The fluid pump of claim 5, wherein a diameter change of the rotor is caused by a length change of the rotor.

7. The fluid pump of claim 6, wherein at least one impeller blade of the rotor is stretched in the longitudinal direction of the rotor by the longitudinal stretching of the rotor.

8. The fluid pump of claim 7, wherein the at least one impeller blade of the rotor is compressed onto the hub by the longitudinal stretching of the rotor.

9. The fluid pump of claim 1, wherein the pump further comprises a pump housing surrounding the rotor and at least one impeller blade.

10. The fluid pump of claim 9, wherein the first element is coupled to the rotor via the pump housing.

11. The fluid pump of claim 10, wherein the pump housing is stretchable in the direction of the longitudinal axis.

12. The fluid pump of claim 11, wherein the at least one impeller blade is configured to expand to an operational state under fluid counter pressure.

13. The fluid pump of claim 12, wherein the pump housing is sized to fit the expanded rotor when the pump housing is not stretched in the direction of the longitudinal axis.

14. The fluid pump of claim 9, wherein the hollow tube further comprises an inflow funnel.

15. The fluid pump of claim 14, wherein the inflow funnel is configured to compress the pump housing.

16. The fluid pump of claim 15, wherein the rotor at least partly loses its shape stability due to longitudinal stretching.

17. The fluid pump of claim 1, wherein the rotor and the at least one impeller blade are formed at least in part by an elastomer.

18. The fluid pump of claim 1, wherein the second element is a drive shaft.

19. The fluid pump of claim 1, wherein the first element is a distal bearing.

* * * * *

UNITED STATES PATENT AND TRADEMARK OFFICE
CERTIFICATE OF CORRECTION

PATENT NO. : 10,316,853 B2  
APPLICATION NO. : 15/236763  
DATED : June 11, 2019  
INVENTOR(S) : Thomas Toellner Page 1 of 1

It is certified that error appears in the above-identified patent and that said Letters Patent is hereby corrected as shown below:

In the Specification

Column 5, Line 36, delete "impeller blade." and replace with --impeller blades.--

Column 5, Line 47, delete "14°" and replace with --14'--

In the Claims

Column 8, Line 52, delete "through going" and replace with --throughgoing--

Signed and Sealed this  
Sixth Day of August, 2019

Andrei Iancu  
*Director of the United States Patent and Trademark Office*